United States Patent [19]

Breslin et al.

[11] Patent Number: 5,268,373
[45] Date of Patent: Dec. 7, 1993

[54] GUANIDINE DERIVATIVES, COMPOSITIONS AND USE

[75] Inventors: Henry J. Breslin, Lansdale; Michael J. Kukla, Maple Glen; Chris R. Rasmussen, Lansdale; Robert W. Tuman, Chalfont, all of Pa.

[73] Assignee: McNeilab, Inc., Spring House, Pa.

[21] Appl. No.: 921,543

[22] Filed: Jul. 28, 1992

[51] Int. Cl.$^5$ ............... A61K 31/155; A61K 31/535; C07C 279/24; C07D 295/125
[52] U.S. Cl. .............................. 514/231.8; 514/237.2; 514/238.5; 514/634; 564/238; 544/86; 544/129; 544/165
[58] Field of Search .......... 544/86, 129, 165; 564/238; 514/231.8, 237.2, 238.5, 634

[56] References Cited

U.S. PATENT DOCUMENTS 4,211,867  7/1980  Rasmussen ............. 544/60
4,269,837  5/1981  Watt et al. ............. 564/238

Primary Examiner—Robert W. Ramsuer
Attorney, Agent, or Firm—Joseph J. Brindisi

[57] ABSTRACT

This invention relates to new heterocyclic derivatives of guanidine and more particularly to such derivatives which have hypoglycemic activity, their methods of use for treating hyperglycemia and novel intermediate compounds for their preparation.

15 Claims, No Drawings

GUANIDINE DERIVATIVES, COMPOSITIONS AND USE

FIELD OF THE INVENTION

This invention relates to new heterocyclic derivatives of guanidine and more particularly to such derivatives which have hypoglycemic activity.

BACKGROUND OF THE INVENTION

Treatment of non-insulin dependent diabetes mellitus (NIDDM) and hyperglycemia associated therewith is directed towards restoring nomaglycemia by improving insulin secretion and reducing insulin resistance. Reduction of blood glucose currently relies on diet and weight control, oral hypoglycemic agents (notably sulfonylureas and biguanides), and insulin. While this triad of therapeutic approaches may provide the desired benefits on a short-term basis, substantial numbers of patients often fail on diet and sulfonylureas, resulting in inadequate glycemic control. Therefore, newer therapeutic agents are needed which can provide greater effectiveness in the treatment of NIDDM.

Linogliride (U.S. Pat. No. 4,211,867), is an effective hypoglycemic agent, whose structure is depicted below:

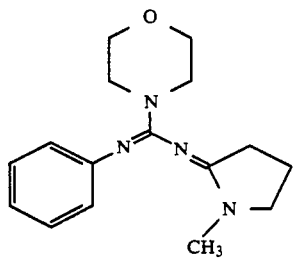

It is an object of the present invention to prepare novel hypoglycemic agents with equal or better efficacy than linogliride for treating hyperglycemia. Additional objects and advantages of the invention will be set forth, in part, in the description which follows and in part will be obvious from this description, or may be learned by practice of the invention. The objects and advantages of this invention are realized and obtained by means of the compositions, methods and the combinations particularly pointed out in the appended claims.

SUMMARY OF THE INVENTION

To achieve the objects in accordance with the purposes of the invention, as embodied and fully described herein the present invention is directed to new heterocyclic derivatives of guanidine which exhibit hypoglycemic activity having the formula I:

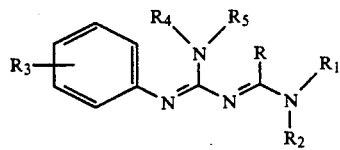

wherein:

R is selected from the group consisting of H, alkyl ($C_1$-$C_8$), branched alkyl ($C_3$-$C_5$), cycloalkyl ($C_3$-$C_7$), aryl (preferably naphthyl or phenyl and more preferably phenyl) and aralkyl wherein the aryl portion is preferably phenyl or naphthyl and the alkyl portion is preferably $C_1$-$C_5$;

$R_1$ and $R_2$ are selected from the group consisting of hydrogen, alkyl ($C_1$-$C_5$), branched alkyl ($C_3$-$C_5$), cycloalkyl ($C_3$-$C_7$) aralkyl wherein the alkyl portion is $C_1$-$C_5$ or hydroxyalkyl wherein the aryl portion is phenyl or substituted phenyl wherein the substituents are selected from alkyl ($C_1$-$C_5$), alkoxy ($C_1$-$C_4$) and halogen such as Br, F or Cl, or $R_1R_2N$ may be taken together to form a heterocyclic ring containing 3-5 carbon atoms where said ring may contain N and one or more (preferably 1-3) heteroatoms such as O or S;

$R_3$ is selected from the group consisting of hydrogen alkyl ($C_1$-$C_5$), alkoxy ($C_1$-$C_4$) and halogen such as Br, F or Cl, preferably $R_3$ is methyl, methoxy or F;

$R_4$ and $R_5$ are the same or different and are selected from the group consisting of alkyl ($C_1$-$C_5$), branched alkyl ($C_3$-$C_5$), cyclohexyl, cyclopentyl or $R_4R_5N$ may be taken together to form a heterocyclic ring containing 3-5 carbon atoms where said ring may contain N and one or more (preferably 1-3) heteroatoms such as O,N or S to form heterocyclic rings preferably piperidino, morpholino, pyrrolidino and thiomorpholino, particularly morpholino.

The present invention is not restricted to the stereoisomer configuration depicted by Formula I but also includes other stereoisomers and tautomers of I which may exist. The invention also includes substantially pure stereochemical isomers and tautomers of the above-described compounds for which such enantiomers exist and can be isolated as would be known to those skilled in the art. The present invention further includes pharmaceutically acceptable salts of the above-described compounds.

As embodied and described herein, the invention further comprises methods of treating hyperglycemia comprising the steps of administering a therapeutically or blood glucose lowering effective amount of one or more hypoglycemic agents of Formula I to a patient suffering from a hyperglycemic condition. Effective dosage amounts will vary in accordance with particular circumstances relating to the patient and condition being treated as would be determined by those skilled in the art.

As embodied and described herein, the invention further comprises novel intermediate compounds for preparing the hypoglycemic agents of Formula I. These novel intermediates have the formulae indicated below where R and $R_{3-5}$ are as described above for Formula I:

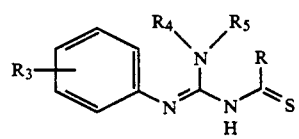

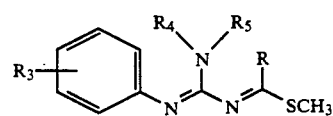

It is to be understood that both the foregoing general and the following detailed description are exemplary and explanatory only and are not intended to be restrictive of the invention as claimed.

DETAILED DESCRIPTION OF THE INVENTION

Reference will now be made in detail to certain preferred embodiments of the invention; examples of which are illustrated below.

The hypoglycemic agents of Formula I can be prepared in accordance with the reaction scheme described below. It should be noted that due to the presence of basic nitrogen in the compounds of Formula I, acid addition thereto produces pharmaceutically acceptable salts which are included in the scope of this invention. Methods of preparation of such salts are discussed below, or are within the knowledge of those skilled in the art.

Guanidine derivative II, which is prepared as described in U.S. Pat. No. 4,211,867, the entire disclosure of which is hereby incorporated herein by reference, is treated with a suitable anhydride such as acetic anhydride and an appropriate base such as potassium carbonate in a suitable solvent such as methylene chloride at room temperature for 30 minutes to 3 hours to give the amide derivative III. Compound III can be treated with a sulfur source such as Lawesson's reagent, in a suitable solvent such as tetrahydrofuran (THF) at 0°-5° C. and stirred for 1-16 hours to give the thioamide derivative IV. Alkylation of IV with a suitable alkylating agent such as methyl iodide and an appropriate base such as sodium hydride in a suitable solvent such as dimethylformamide (DMF) at 0° C. to room temperature for 1-16 hours gives the alkylated derivative V. Compound V can be treated with an excess of a suitable amine in an appropriate solvent such as tetrahydrofuran (THF), at 0° C. to 100° C. for 1 hour to 30 days to give the substituted carboximidamides or guanidine derivatives I.

Alternatively, the amide derivative VI, can be treated with Meerwein's Reagent to give an imidate which is treated with guanidine derivative II in an appropriate solvent, such as methylene chloride at room temperature to reflux for 1 hour to 12 days to give the substituted carboximidamides I. The amide derivative VI can be treated with phosgene in a suitable solvent such as toluene at 0° C. to reflux for 1-5 hours; followed by the addition of guanidine derivative II in a suitable solvent such as methylene chloride and stirring at room temperature for 5-16 hours to give the substituted carboximidamides I. Further, treatment of the amide derivative VI with dimethyl sulfate at 100° C. followed by the addition of the guanidine derivative II also gives the substituted carboximidamides I.

Treatment of a suitable nitrile derivative VII, such as isobutylnitrile with an appropriate trialkyloxonium fluoroborate salt such as triethyloxonium tetrafluoroborate in a suitable solvent such as methylene chloride at reflux for 4-6 hours gives the nitrilium salt derivative VIII. Treatment of said salt with guanidine derivative II at reflux for 16 hours gives the substituted carboximidamides I.

Therapeutically active non-toxic addition salts of carboximidamides I, were prepared by treatment of I with appropriate organic and inorganic acids such as hydrochloric, fumaric, saccharin, sulfuric, nitric, phosphoric, acetic, glycolic, pyruvic, mandelic, oxalic and the like in a suitable solvent.

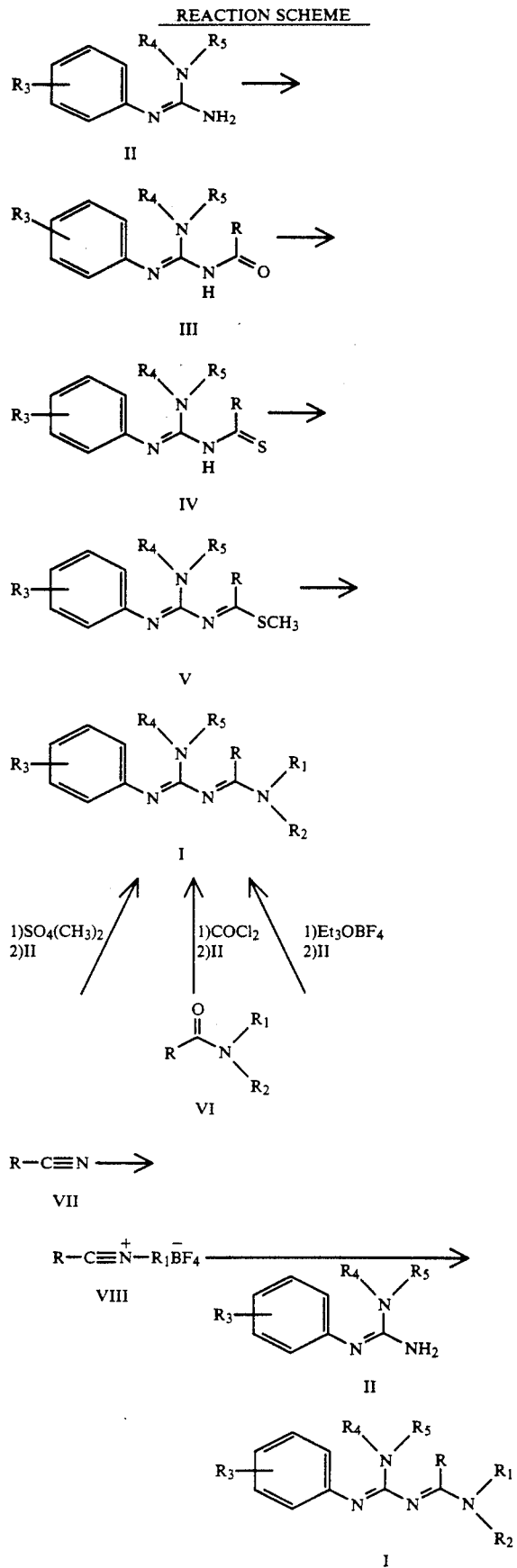

As described above the compound of Formula II is known and is used as a starting material for producing the intermediate compounds of Formula III, IV and V.

The invention will now be illustrated by examples. The following examples describe the invention in greater particularity and are intended to be a way of illustrating but not limiting of the scope of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

EXAMPLES

The following processes and procedures for preparing the compounds of the present invention are identified in the reaction schemes illustrated above. The schemes and the specific examples below describe with particularity the various chemical reactions and procedures utilized. Any methods, starting materials or reagents which are not particularly described are those which are known to those skilled in the art.

Melting point determinations were carried out on a Thomas Hoover capillary melting point apparatus and are uncorrected. All final compounds had spectra (elemental analysis) consistent with their assigned structures. The elemental analysis were measured on a Perkin Elmer 2400 spectrometer. All column chromatography were run using Silica Gel 60, 230–400 mesh and an appropriate commercially available solvent. Unless otherwise noted, the materials used in the examples were obtained from readily available commercial suppliers or synthesized by standard methods known to anyone skilled in the art of chemical synthesis. The substituent groups, which vary between examples are assumed to be hydrogen unless otherwise noted. The examples identified with a Cpd # correspond to those identified in the compound activity table (Table 5).

EXAMPLE 1

N-[(4-Morpholinyl)(phenylimino)methyl]acetamide

A solution of acetic anhydride (4.4 mL, 45 mM) in methylene chloride (60 mL) was added over 30 minutes to a stirred mixture of guanidine derivative II ($NR_4R_5=$ morpholine 9.2 g, 45 mM, See U.S. Pat. No. 4,211,867, and potassium carbonate (6.4 g, 45 mM) in methylene chloride (80 mL). The resulting mixture was stirred for 2.5 hours and washed with several portions of 15% NaOH (aq) solution. The combined aqueous extracts were saturated with NaCl and extracted several times with $CHCl_3$. The combined organic extracts were dried ($K_2CO_3$), filtered, and concentrated in vacuo to give the amide III ($R=CH_3$) as a solid: mp 92°–95° C. Using the general procedure above but utilizing different anydrides the compounds listed in Table 1 were synthesized.

TABLE 1

| R | mp (°C.) |
|---|---|
| n-$C_6H_{11}$ | 69–76 |
| $C_2H_5$ | 105–108 |
| i-$C_3H_7$ | Not Available (N.A.) |

EXAMPLE 2

N-[(4-Morpholinyl)(phenylimino)methyl]ethanethioamide•HCl

Lawesson's reagent (16.48 g, 41.20 mM) was added to a stirred solution of amide III ($R=CH_3$, $NR_4R_5=$ morpholine: 18.57 g, 74.9 mM) in THF at 0°–5° C. under $N_2$. The mixture was stirred for 3.5 hours at 0°–5° C. and for 16 hours at room temperature. The resulting oil was dissolved in acetone (150 mL) and treated with ether/HCl. The thioamide IV was isolated as its HCl salt from the treated oil as a solid, mp 181°–184° C.

The following general procedure was used in the synthesis of the compounds listed in Table 2.

Lawesson's reagent (1 molar equivalent) was added to a stirred solution of amide III (2 molar equivalents) in a suitable solvent at 0°–5° C. under $N_2$. The mixture was stirred for 3–5 hours at 0°–5° C. and for 16–72 hours at room temperature. The resulting oil was purified by any of the standard techniques which include chromatography and recrystallization to give the thioamide derivative IV. HCl salts are obtained by treating the product compounds with HCl in an appropriate solvent, e.g. ether.

TABLE 2

| R | mp (°C.) |
|---|---|
| n-$C_6H_{11}$ | (oil) |
| $C_2H_5$ (HCl Salt) | 176–179 |
| i-$C_3H_7$ (HCl Salt) | N.A. |

EXAMPLE 3

N-[1-(Methylthio)ethylidene]-N'-phenyl-4-morpholinecarboximidamide

The HCl salt of thioamide IV ($R=CH_3$, $NR_4R_5=$ morpholine: 17.94 g, 60 mM) was added to a suspension of hexane washed sodium hydride (50% oil dispersion: 5.76 g, 120 mM) in THF (140 mL) at 0° C. under $N_2$. The resulting mixture was stirred for 25 minutes at 0° C. and for 2 hours at room temperature. Methyl iodide (3.72 mL, 60 mM) was added, and the resulting mixture was stirred for 2 hours at room temperature and concentrated in vacuo. Aqueous NaOH (15%) and methylene chloride were added to the residue. The organic layer was washed with successive portions of 15% NaOH (aq) and brine, dried ($K_2CO_3$), filtered, and concentrated in vacuo to give the thiomethyl derivative V (14.26 g, 86%) as an oil which crystallized upon standing.

The following general procedure was used in the synthesis of the compounds listed in Table 3:

The thioamide derivative IV (1 molar equivalent) was added to a suspension of hexane washed sodium hydride (50% oil dispersion: 1–2 molar equivalents) in THF at 0° C. under $N_2$. The resulting mixture was stirred at 0° C. and at room temperature. Methyl iodide (1–4 molar equivalents) was added, and the resulting mixture was stirred at room temperature and concentrated in vacuo. Aqueous base and a suitable organic solvent were added to the residue. The organic layer was washed with successive portions of aqueous base and brine, dried ($K_2CO_3$) and concentrated in vacuo to give the thiomethyl derivative V, which was used without further purification.

TABLE 3

| R |
|---|
| $C_6H_{11}$ |
| $C_2H_5$ |
| $i\text{-}C_3H_7$ |

EXAMPLE 4

N-[1-(Piperidinyl)ethylidene]-N'-phenyl-4-morpholinecarboximidamide(E)-2-Butenedioate Cpd 5

Thiomethyl derivative V (R=$CH_3$, $NR_4R_5$= morpholine: 1.85 g, 6.67 mM) was added to a solution of piperidine (66 mL, 6.67 mM) in THF (70 mL) and the mixture was stirred at room temperature for 48 hours and at reflux for another 48 hours under $N_2$. The reaction mixture was concentrated in vacuo, partitioned between methylene chloride and 15% NaOH (aq). The resulting organic layer was dried ($K_2CO_3$), concentrated in vacuo and dissolved in acetonitrile (10 mL). A solution of fumaric acid (0.69 g, 5.9 mM) in isopropanol (20 mL) was added to the acetonitrile solution followed by the addition of a portion of ether. The title compound precipitated out of this mixture as a solid: mp 154°–157° C.

Anal. Calc'd for $C_{18}H_{26}N_4O/C_4H_4O_4$: C, 61.38; H, 7.02; N, 13.01 Found: C, 61.19; H, 7.03; N, 12.96.

EXAMPLE 5

N-[1-(Butylmethylamino)ethylidene]-N'-phenyl-4-morpholinecarboximidamide(E)-2-Butenedioate Ethanolate (1:1:1) Cpd 9

Thiomethyl derivative V (R=$CH_3$, $NR_4R_5$= morpholine: 2.65 g, 9.57 mM) was added to a solution of N-methyl-N-butylamine (8.34 g, 95.7 mM) in THF (20 mL) and was stirred at room temperature under $N_2$ for 84 hours. The reaction mixture was concentrated in vacuo and partitioned between methylene chloride and 15% NaOH (aq). The resulting organic layer was dried ($K_2CO_3$), and concentrated in vacuo. The residue was dissolved in ether (30 mL), filtered through Decalite, and added to a solution of fumaric acid in EtOH. The title compound precipitated as a solid: mp 94°–99° C.

Anal. Calc'd for $C_{18}H_{28}N_4O/C_4H_4O_4/C_2H_6O$: C, 60.23; H, 8.00; N, 11.71 Found: C, 60.16; H, 7.71; N, 12.05.

EXAMPLE 6

N-[1[(1-Methylethyl)amino]ethylidene]-N'-phenyl-4-morpholinecarboximidamide Cpd 10

Thiomethyl derivative V (R=$CH_3$, $NR_4R_5$= morpholine: 4.71 g, 17.4 mM) was added to isopropylamine (30 mL, 353 mM) and stirred at room temperature for 16 hours and at 45° C. for another 84 hours in a pressure bottle. The reaction mixture was concentrated in vacuo, partitioned between methylene chloride and 15% NaOH (aq). The resulting organic layer was dried ($K_2CO_3$), filtered, and concentrated in vacuo. The residue was triturated with ether and followed by trituration with hexane. The title compound was isolated from this mixture as a white solid: mp 142°–145° C.

Anal. Calc'd for $C_{16}H_{24}N_4O$: C, 66.64; H, 8.39; N 19.43 Found: C, 66.45; H, 8.40; N, 19.27.

EXAMPLE 7

N-[1-(Morpholinyl)ethylidene]-N'-phenyl-4-morpholinecarboximidamide(E)-2-Butenedioate Ethanolate (3:3:1) Cpd 19

Thiomethyl derivative V (R=$CH_3$, $NR_4R_5$= morpholine: 1.40 g, 5.00 mM) was added to a solution of morpholine (10 mL, 115 mM) in THF (40 mL) and was stirred at 60° C. for 72 hours under $N_2$. The reaction mixture was concentrated in vacuo and partitioned between methylene chloride and 15% NaOH (aq). The resulting organic layer was dried ($K_2CO_3$), filtered, and concentrated in vacuo. A solution of fumaric acid (0.69 g, 5.95 mM) in EtOH (20 mL) was added to a solution of the residue (1.93 g) in EtOH. The title compound precipitated out of this mixture as a solid: mp 185°–187° C.

Anal. Calc'd for $C_{18}H_{26}N_4O/C_4H_4O_4/0.33\ C_2H_6O$: C, 58.11; H, 6.75; N, 12.51 Found: C, 57.96; H, 6.79; N, 12.50.

EXAMPLE 8

N'-Phenyl-N-[1-[(phenylmethyl)amino]ethylidene]-4-morpholinecarboximidamide Cpd 22

Thiomethyl derivative V (R=$CH_3$, $NR_4R_5$= morpholine: 1.51 g, 5.45 mM) was added to benzylamine (6.00 mL, 54.9 mM) and stirred at room temperature for six days under $N_2$. The resulting mixture was diluted with chloroform and washed several times with 3N HCl. The organic layer was extracted with 3N NaOH (aq), dried ($K_2CO_3$), filtered, concentrated and triturated with hexane. The title compound was isolated from the treated residue as a solid: mp 126°–129° C.

Anal. Calc'd for $C_{20}H_{24}N_4O$: C, 71.40; H, 7.19; N, 16.65 Found: C, 71.34; H, 7.21N, 16.66.

EXAMPLE 9

N'-Phenyl-N-[1-(n-propylamino)ethylidene]-4-morpholinecarboximidamide Cpd 24

Thiomethyl derivative V (R=$CH_3$, $NR_4R_5$= morpholine: 2.00 g, 7.22 mM) was added to n-propylamine (20 mL, 243 mM) and stirred at room temperature for 72 hours. The resulting mixture was concentrated in vacuo and crystallized from cyclohexane to give the title compound as a solid: mp 101°–103° C.

Anal. Calc'd for $C_{16}H_{24}N_4O$: C, 66.64; H, 8.39; N, 19.43 Found: C, 66.71; H, 8.39; N, 19.40.

EXAMPLE 10

N-[1-(Dimethylamino)ethylidene]-N'-phenyl-4-morpholinecarboximidamide(E)-2-Butenedioate (2:3) Cpd 3

Dimethylamine was bubbled into a solution of the thiomethyl derivative V (R=$CH_3$, $NR_4R_5$= morpholine: 2.77 g, 10.00 mM) in THF (200 mL) at room temperature for 15 minutes. The resulting mixture was stirred at room temperature for 16 hours, concentrated in vacuo, and partitioned between chloroform and 15% NaOH (aq). The resulting organic layer was dried ($K_2CO_3$), filtered, and concentrated in vacuo. The resulting oil was triturated with $Et_2O$ to give a white solid. This solid was dissolved in EtOH and combined with a solution of fumaric acid with EtOH. The title compound precipitated as a solid: mp 150°–151° C.

Anal. Calc'd for $C_{15}H_{22}N_4O/(3/2):C_4H_4O_4$: C, 56.24.; H, 6.29; N, 12.47 Found: C, 56.28; H, 6.36; N, 12.45.

The following general procedure was used to synthesize the compounds listed in Table 4:

Dimethylamine was bubbled into a solution of the thiomethyl derivative V in THF at 0° C. to room temperature for 10–30 minutes. The resulting mixture was stirred at room temperature for 16–72 hours concentrated in vacuo, and partitioned between chloroform and 15% NaOH (aq). The organic layer was dried ($K_2CO_3$), filtered, concentrated in vacuo and dissolved in a suitable solvent. A solution of fumaric acid in an appropriate solvent was added to a solution of the residue in a suitable solvent. The desired carboximidamide I, precipitated as the solid fumaric salt.

TABLE 4

| | R | $R_1$ | $R_2$ | mp °C. | Elemental Analysis | | |
|---|---|---|---|---|---|---|---|
| | | | | | C | H | N |
| Cpd 4 | $C_2H_5$ | $CH_3$ | $CH_3$ | 141–144 | 59.22 | 6.95 | 13.81 |
| Cpd 8 | n-$C_6H_{13}$ | $CH_3$ | $CH_3$ | 140–143.5 | 60.25 | 7.49 | 10.74 |

EXAMPLE 11

N-[1-(Ethylamino)ethylidene]-N'-phenyl-4-morpholinecarboximidamide(E)-2-Butenedioate Cpd 30

Ethylamine was bubbled into a stirred solution of the thiomethyl derivative V (R=$CH_3$, $NR_4R_5$= morpholine: 2.00 g, 7.22 mM) in THF (100 mL) for 10 minutes twice over a 12 day period. The resulting mixture was concentrated in vacuo. A solution of fumaric acid in isopropanol was added to a solution of the residue in isopropanol. The title compound precipitated as a solid: mp 155.5°–158.5° C.

Anal. Calc'd for $C_{15}H_{22}N_4O/C_4H_4O_4$: C, 58.45; H, 6.71; N, 14.35 Found: C, 58.36; H, 6.76; N, 14.28

EXAMPLE 12

N-[1-[(1,1-Dimethylethyl)amino]ethylidene]-N'-phenyl-4-morpholinecarboximidamide Cpd 21

The thiomethylderivative V (R=$CH_3$, $NR_4R_5$= morpholine: 1.94 g, 7.00 mM) was dissolved in t-butylamine (100 mL), placed in a pressure bottle and heated from 60°–75° C. for 26 days. The resulting mixture was concentrated in vacuo and partitioned between $CH_2Cl_2$ and water. The organic layer was dried ($K_2CO_3$), filtered, and concentrated in vacuo. The treated residue was triturated with ether/cyclohexane and recrystalized from ether to give the title compound as a solid: mp 164°–166.5° C.

Anal. Calc'd for $C_{17}H_{26}N_4O$: C, 67.52; H, 8.67; N, 18.53 Found: C, 67.53; H, 8.67; N, 18.51.

EXAMPLE 13

N'-Phenyl-N-[1-[phenyl(phenylmethyl)amino]ethylidene]-4 morpholinecarboximidamide Compound with 1,2-Benzisothiazol-3(2H)-one, 1, 1 Dioxide Cpd 15

A solution of N-benzyl-N-phenylacetamide (JACS 1953, 75, 744: 17.94 g, 79.73 mM) in methylene chloride (200 mL) was added to freshly prepared $Et_3O(+)BF_4(-)$ (Organic Syntheses 1966, 46, 113–115: $Et_2OBF_3$ 35.3 mM, epichlorohydrin 26.5 mM, ether 300 mL) at room temperature under Ar. The reaction mixture was stirred at room temperature for 3 hours. A solution of guanidine derivative II ($NR_4R_5$= morpholine: 16.35 g, 79.73 mM) in methylene chloride (150 mL) was added to the reaction mixture and stirred at room temperature for 72 hours. The resulting mixture was washed with successive portions of water and 15% NaOH (aq). The organic layer was separated, dried ($K_2CO_3$), filtered, and concentrated in vacuo. A solution of saccharin in EtOH was added to an equimolar portion of the treated residue which was dissolved in EtOH. The title compound precipitated as a white solid: mp 170°–173° C.

Anal. Cal'd for $C_{26}H_{28}N_4O/C_7H_5NO_3S$: C, 66.54.; H, 5.58; N, 11.76 Found: C, 66.49; H, 5.73; N, 11.85.

EXAMPLE 14

N'-Phenyl-N-[1-(phenylamino)ethylidene]-4-morpholinecarboximidamide Compound with 1,2-Benzisothiazol-3(2H)-one, 1, 1 Dioxide Cpd 16

10% Palladium on carbon (1.95 g) and conc. HCl (3 mL) were added to a solution of N'-phenyl-N-[1-[phenyl(phenylmethyl)amino]-ethylidene]-4-morpholinecarboximidamide (9.75 g, 23.56 mM) in EtOH (150 mL). The resulting mixture was placed in a Parr Bottle and pressurized with $H_2$ for 48 hours. The reaction mixture was filtered through Decalite and concentrated in vacuo. The residue was partitioned between water and methylene chloride. The organic extract was washed with 15% NaOH (aq), dried ($K_2CO_3$), filtered and concentrated in vacuo. The treated residue was dissolved in EtOH (10 mL) and added to a solution of saccharin (1.83 g) in EtOH (15 mL). The title compound precipitated out of this mixture as a solid: mp 180°–181.5° C.

Anal. Calc'd for $C_{19}H_{22}N_4O/C_7H_5NO_3S$: C, 61.77; H, 5.38; N, 13.85 Found: C, 61.69; H, 5.43; N, 13.83.

EXAMPLE 15

N-[1-Aminoethylidene]-N'-phenyl-4-morpholinecarboximidamide Cpd 23

A solution of acetamide (1.35 g, 22.55 mM) in methylene chloride (50 mL) was added to freshly prepared $Et_3O(+)BF_4(-)$, ($Et_2OBF_3$ 35.3 mM, epichlorohydrin 26.5 mM, ether 300 mL) at room temperature under Ar. The reaction mixture was stirred at room temperature for 16 hours. Guanidine derivative II ($NR_4R_5$= morpholine: 4.62 g, 22.5 mM) was added to the reaction brew and stirred at room temperature for 72 hours. The resulting mixture was washed with 15% NaOH (aq) and the organic layer was separated, dried ($K_2CO_3$), filtered, and concentrated in vacuo. The residue was purified by column chromatography using ammonium hydroxide and methanol as eluents followed by recrystallization of the desired fractions from cyclohexane to give the title compound as a solid: mp 146°–148° C.

Anal. Calc'd for $C_{13}H_{18}N_4O$: C, 63.39; H, 7.37; N, 22.75 Found: C, 63.23; H, 7.44; N, 22.66.

EXAMPLE 16

N-[1-(2-Hydroxyethyl)aminoethylidene]-N'-phenyl-4-morpholinecarboximidamide Cpd 31

A solution of the amide derivative VI (R=$CH_3$, $R_1$=—$(CH_2)_2OH$: 3.36 g, 22.5 mM) in methylene chloride (20 mL) was added to freshly prepared 1N $Et_3O(+)BF_4$ (—)/methylene chloride (100 mL) at 0° C. under Ar. The reaction mixture was warmed to room temperature and stirred for 16 hours. Guanidine derivative II ($NR_4R_5$= morpholine: 4.62 g, 22.5 mM) was added to the reaction brew and the resulting mixture was stirred at room temperature for 16 hours and at 45° C. for an additional 6 days. The resulting mixture was washed with 15% NaOH (aq). and the organic layer was separated, dried (K₂CO₃) and concentrated in vacuo. The residue was purified by column chromatography using ammonium hydroxide and methanol as eluents followed by crystallization of the desired fractions from ether to give the title compound as a solid: mp 132°-134° C.

Anal. Calc'd for $C_{15}H_{22}N_4)_2$: C, 62.05; H, 7.64; N, 19.30 Found: C, 62.06; H, 7.65; N, 19.26.

EXAMPLE 17

N-[1-(Methylphenylamino)ethylidene]-N'-phenyl-4-morpholinecarboximidamide (E)-2-Butenedioate Hydrate (2:2:1) Cpd 11

N-Methyl-N-phenylacetamide (13.6 g, 90 mM) and dimethyl sulfate (8.4 mL, 90 mM) were heated on a steam bath under N₂ until crystals began to form inside the reaction vessel. A solution of guanidine derivative II (R=CH₃, NR₄R₅= morpholine: 18.45 g, 90 mM) in methylene chloride (140 mL) was added to the mixture and the resulting mixture was stirred at room temperature for 1 hour. The reaction mixture was filtered and the filtrate was partitioned between 3N HCl and ether. The aqueous layer was extracted with several portions of chloroform and the combined chloroform extracts were washed with 15% NaOH (aq), dried (K₂CO₃), filtered and concentrated in vacuo. The residue was dissolved in ether (50 mL), filtered through Decalite, and added to a solution of fumaric acid (3.85 g) in EtOH (100 mL). The title compound precipitated as a white solid: mp 160°-161.5° C.

Anal. Calc'd for $C_{20}H_{24}N_4O/C_4H_4O_4/0.5\ H_2O$: C, 62.41; H, 6.34; N, 12.13 Found: C, 62.49; H, 6.41; N, 12.10.

EXAMPLE 18

N-[1-(Methylamino)ethylidene]-N'-phenyl-4-morpholinecarboximidamide (E)-2-Butenedioate (2:3) Cpd 7

Monomethylamine was bubbled into a solution of the thiomethyl derivative V (R=CH₃, NR₄R₅=morpholine: 1.10 g, 3.99 mM) in THF (60 mL) for 15 minutes and the resulting mixture was stirred at room temperature in a stoppered flask for 24 hours. An additional portion of monomethylamine was bubbled into the reaction mixture and the mixture was stirred for another 24 hours. The resulting mixture was concentrated in vacuo and partitioned between 15% NaOH (aq) and methylene chloride. The organic layer was dried (K₂CO₃), filtered, and concentrated in vacuo. A solution of the residue in isopropanol was added to a solution of fumaric acid in isopropanol. The title compound precipitated as a white solid: mp 145°-147° C.

Anal. Calc'd for $C_{14}H_{20}N_4O/C_4H_4O_4(2:3)$: C, 55.29; H, 6.03; N, 12.90 Found: C, 55.14; H, 6.05; N, 12.86.

EXAMPLE 19

N-[1-(Dimethylamino)-2-methylpropylidene]-N'-phenyl-4-morpholinecarboximidamide Cpd 6

Dimethylamine was bubbled (15 minutes) into a solution of freshly prepared alkylated thio derivative V (R=i-Pr, Nr₄R₅=morpholine: 10 mM) in THF (70 mL). The resulting mixture was placed in a pressure bottle, heated from 50°-68° C. for five days and concentrated in vacuo. The treated residue was partitioned between 15% NaOH (aq) and chloroform, and the resulting organic layer was dried (K₂CO₃), filtered, and concentrated in vacuo. Crystallization of the residue from hexane afforded the title compound as a solid: mp 88°-90° C.

Anal. Calc'd for $C_{17}H_{26}N_4O$: C, 67.52; H, 8.67; N, 18.53 Found: C, 67.54; H, 8.69; N, 18.51.

EXAMPLE 20

N-[2-Methyl-1-(methylamino)propylidene]-N'-phenyl-4-morpholinecarboximidamide Cpd 13

Methylamine was bubbled (15 minutes) into a solution of freshly prepared alkylated thio derivative V (R=i-Pr, NR₄R₅=morpholine: 11.87 mM) in THF (100 mL). The resulting mixture was stoppered and stirred at room temperature for 72 hours. Another portion of methylamine was bubbled (15 minutes) into the reaction mixture and the resulting mixture was stirred for another 48 hours. The mixture was concentrated in vacuo and partitioned between 15% NaOH (aq) and methylene chloride. The organic layer was dried (K₂CO₃), filtered, and concentrated in vacuo. The treated residue was crystallized from ether to give the title compound as a solid: mp 155°-157° C.

Anal. Calc'd for $C_{16}H_{24}N_4O$: C, 66.64; H, 8.39; N, 19.43 Found: C, 66.52; H, 8.42; N, 19.37.

EXAMPLE 21

N-[2-Methyl-1-[(1-methylethyl)amino]propylidene]-N'-phenyl-4-morpholinecarboximidamide Cpd 18

Freshly prepared alkylated thio derivative V (R=i-Pr, NR₄R₅=morpholine: 1.20 g, 3.93 mM) was added to isopropylamine (100 mL); and the mixture was stoppered and stirred at 62° C. for 16 hours. The resulting mixture was concentrated in vacuo and partitioned between 15% NaOH (aq) and ether. The organic layer was dried (K₂CO₃), filtered through Decalite and concentrated in vacuo. The residue was recrystallized from cyclohexane to give the title compound as a solid: mp 132°-135° C.

Anal. Calc'd for $C_{18}H_{28}N_4O$: C, 68.32; H, 8.92; N, 17.71 Found: C, 68.39; H, 9.01; N, 17.59.

EXAMPLE 22

N-[1-(Ethylamino)-2-methylpropylidene]-N'-phenyl-4-morpholinecarboximidamide Cpd 26

Meerwein's reagent (1 molar in methylene chloride; 47.2 mL) was added to isobutylnitrile (1.7 g, 25 mM) and the resulting mixture was heated to reflux for 23 hours. Guanidine derivative II (NR₄R₅=morpholine: 2.5 g, 12.2 mM) was added to the reaction and the resulting mixture was heated at reflux for another 6 hours and stirred at room temperature overnight. The reaction was quenched with saturated NaHCO₃ and the resulting organic layer was separated and washed with another portion of saturated NaHCO₃. The organic phase was dried (MgSO₄), filtered and concentrated in vacuo. The residue was recrystallized from isopropanol and toluene. The resulting solid was partitioned between 3N NaOH and methylene chloride. The resulting organic layer was dried (MgSO₄), filtered, and concentrated in vacuo to give the title compound as a solid: mp 155°-158° C.

Anal. Calc'd for $C_{17}H_{26}N_4O$: C, 67.52; H, 8.67; N, 18.53 Found: C, 66.32; H, 8.61; N, 18.20.

EXAMPLE 23

N'-[4-Fluorophenyl]-N-[2-methyl-1-(methylamino)-propylidene]-4-morpholinecarboximide Cpd 28

Trimethyloxonium tetrafluoroborate (10.42 g, 70.4 mM) was added to a solution of isobutylnitrile (7.3 mL, 80.6 mM) in methylene chloride (55 mL), and the resulting mixture was heated to reflux for 36 hours. This reaction mixture was added to a solution of the fluoroguanidine derivative II ($R_3$=4—F, $NR_4R_5$=morpholine: 14.28 g, 64.0 mM) in methylene chloride (60 mL) at 0° C. The resulting mixture was stirred at 0° C. for 5 minutes and at room temperature for 5 hours. The resulting precipitate was filtered and washed several times with methylene chloride. The organic filtrates were combined, cooled to 0° C., basified with 3N NaOH (aq) to a ph>9, dried (MgSO$_4$), filtered, and concentrated in vacuo. The treated residue was crystallized from methylene chloride and hexane to give the title compound as a solid: mp 150°-152° C.

Anal. Calc'd for $C_{16}H_{23}FN_4O$: C, 62.72; H, 7.57; N, 18.28 Found: C, 62.71; H, 7.62; N, 18.24.

EXAMPLE 24

N-[2-Methoxyphenyl]-N-[2-methyl-1-(methylamino)-propylidene]-4-morpholinecarboximide Cpd 33

The title compound was prepared as described in Example 23 starting with trimethyloxonium tetrafluoroborate (13.19 g, 89.2 mM), isobutylnitrile (9.7 mL, 107 mM) and the 2-methoxy-guanidine derivative II ($R_3$=2—OMe, $NR_4R_5$=morpholine, prepared using the methods outlined in U.S. Pat. No. 4,211,867: 29.13 g, 80.2 mM) in methylene chloride to give a solid: mp 149°-151° C.

Anal. Calc'd for $C_{17}H_{26}N_4O_2$: C, 64.12; H, 8.23; N, 17.59 Found: C, 64.07; H, 8.25; N, 17.54.

EXAMPLE 25

N-[2-Methyl-1-(propylamino)propylidene]-N'-phenyl-4-morpholinecarboximidamide Cpd 27

Meerwein's reagent (47.2 mM) dissolved in methylene chloride (100 mL) was added to N-(n-propyl-)isobutyramide (J. Org. Chem 1986, 51(20), 3839–48: 5.2 g, 40 mM), and the resulting mixture was stirred at room temperature for 5 hours. Guanidine derivative II ($NR_4R_5$=morpholine: 8.2 g, 40 mM) was added to the reaction and the resulting mixture was stirred at room temperature for 12 days. A solid precipitate was removed and the filtrate was washed with saturated NaHCO$_3$. The organic phase was dried (MgSO$_4$), filtered, and concentrated in vacuo. The residue was purified by column chromatography on silica gel using methanol/ammonium hydroxide as an eluent and crystallized from hexane to give the title compound as a solid: mp 122.5°-123.5° C.

Anal. Calc'd for $C_{18}H_{28}N_4O$: C, 68.32; H, 8.92; N, 17.71 Found: C, 68.24; H, 8.93; N, 17.68.

EXAMPLE 26

N-[1-Amino-2-methylpropylidene]-N'-phenyl-4-morpholinecarboximidamide Cpd 25

Isobutyramide (3.92 g, 45 mM) was added to freshly prepared $Et_3O(+)BF_4(-)$ $Et_2OBF_3$ 70.6 mM, epichlorohydrin 53 mM, ether 250 mL) at room temperature under Ar. The reaction mixture was stirred at room temperature for 16 hours. The reaction was quenched with 50% Na$_2$CO$_3$ and filtered. The organic layer was separated, dried (K$_2$CO$_3$), concentrated in vacuo and distilled to give the imidate derivative as an oil. This imidate derivative was combined with the guanidine derivative II and THF (10 mL) ($NR_4R_5$=morpholine: 4.0 g, 19.48 mM) and stirred at room temperature for 16 hours and heated from 50°-80° C. for 4 days. Another portion of the imidate (4.78 g, 19.5 mM) was added to the reaction mixture and this mixture was heated at 50°-80° C. for 12 days. The resulting mixture was concentrated in vacuo, and purified by a combination of column chromatography on silica gel using methanol/ammonium hydroxide as an eluent and sequentially crystallized from diethyl ether and cyclohexane to give the title compound as a white solid: mp 123°-126° C.

Anal. Calc'd for $C_{15}H_{22}N_4O$: C, 65.67; H, 8.08; N, 20.42 Found: C, 65.54; H, 8.12; N, 20.35.

EXAMPLE 27

N-[(Dimethylamino)methylene]-N'-phenyl-4-morpholinecarboximidamide Cpd 1

A solution of DMF (9 mL, 112.5 mM) in methylene chloride (75 mL) was added to freshly prepared $Et_3O(+)BF_4(-)$ ($Et_2OBF_3$ 176.0 mM, epichlorohydrin 132.0 mM, ether 500 mL) in methylene chloride (400 mL) at room temperature under Ar. The reaction mixture was stirred at room temperature for 6 hours. A solution of guanidine derivative II ($NR_4R_5$=morpholine: 23.25 g, 112.5 mM) in methylene chloride (100 mL) was added to the reaction brew and stirred at room temperature for 16 hours. The resulting mixture was washed with successive portions of water and 15% NaOH (aq). The organic layer was separated, dried (K$_2$CO$_3$), filtered, and concentrated in vacuo. The residue was purified by trituration with ether to give the title compound as a white solid: mp 109°-112° C.

Anal. Calc'd for $C_{14}H_{20}N_4O$: C, 64.59; H, 7.74; N, 21.52 Found: C, 64.66; H, 7.78; N, 21.52.

EXAMPLE 28

N-[(Dimethylamino)phenylmethylene]-N'-phenyl-4-morpholinecarboximidamide Hydrochloride Cpd 2

Phosgene (2M in toluene: 50 mL) was added to a solution of N'N-dimethylbenzamide (3.4 g, 22.5 mM) and the mixture was heated to reflux for 15 minutes. Another portion of phosgene (20 mL) was added and the resulting mixture was heated to reflux for 50 minutes and concentrated in vacuo. The guanidine derivative II ($NR_4R_5$=morpholine: 4.65 g, 22.5 mM) in methylene chloride (40 mL) was added to a solution of the residue in methylene chloride (30 mL) and the reaction was stirred overnight at room temperature. The resulting mixture was washed with water and the resulting aqueous layer was washed with several portions of chloroform. The combined chloroform extracts were concentrated in vacuo and crystallized from ether to give the title compound as a solid: mp 215°-218° C.

Anal. Calc'd for $C_{14}H_{20}N_4O/HCl$: C, 64.42; H, 6.76; N, 15.02 Found: C, 64.17; H, 6.84; N, 14.99.

EXAMPLE 29

N-[1-(Dimethylamino)-2-phenylethylidene]-N'-phenyl-4-morpholinecarboximidamide(E)-2-Butenedioate (1:1) Cpd 14

A solution of N,N-dimethylphenylacetamide (European Patent No. 86-112499, Sep. 10, 1986: 11.93 g, 73.19 mM) in methylene chloride (150 mL) was added to freshly prepared Et$_3$O(+)BF$_4$(−) (Et$_2$OBF$_3$ 114.52 mM, epichlorohydrin 86.11 mM, ether 250 mL) at room temperature under Ar. The reaction mixture was stirred at room temperature for 3 hours. A solution of guanidine derivative II (NR$_4$R$_5$=morpholine: 15.00 g, 73.19 mM) in methylene chloride (150 mL) was added to the reaction brew and stirred at room temperature for 16 hours. The resulting mixture was washed with successive portions of 3N HCl followed by successive portions of 15% NaOH (aq). The resulting organic layer was dried (K$_2$CO$_3$), filtered, and concentrated in vacuo. A solution of fumaric acid (5.98 g, 51.51 mM) in EtOH (50 mL) was added to a solution of the residue in EtOH (50 mL). The title compound precipitated as a solid: mp 169.5°–171° C.

Anal. Calc'd for C$_{21}$H$_{26}$N$_4$O/C$_4$H$_4$O$_4$: C, 64.36; H, 6.48; N, 12.01 Found: C, 64.27; H, 6.54; N, 11.98.

EXAMPLE 30

N-[1-(Dimethylamino)-2,2-dimethylpropylidene]-N'-phenyl-4-morpholinecarboximidamide Compound with 1,2-Benzisothiazol3(2H)-one, 1,1-dioxide Cpd 17

A solution of N,N-dimethyltrimethylacetamide (J. Org. Chem. 1981, 46, 1597-602: 2.90 g, 22.5 mM) in methylene chloride (60 mL) was added to freshly prepared Et$_3$O(+)BF$_4$(−) (Et$_2$OBF$_3$ 35.3 mM, epichlorohydrin 26.5 mM, ether 75 mL) at room temperature under Ar. The reaction mixture was stirred at room temperature for 4 hours. A solution of guanidine derivative II (NR$_4$R$_5$=morpholine: 4.65 g, 22.5 mM) in methylene chloride (30 mL) was added to the reaction brew and the resulting mixture was stirred at room temperature for 16 hours and concentrated in vacuo. The residue was partitioned between water and ether and the resulting aqueous phase was washed with several portions of methylene chloride. The combined methylene chloride layers were washed with successive portions of water, 3N HCl and 15% NaOH (aq), dried (K$_2$CO$_3$), filtered, and concentrated in vacuo. A solution of saccharin (0.51 g) in EtOH (20-30 mL) was added to a filtered solution of the residue in ether. The title compound precipitated out of this mixture as a white solid: mp 131.5°–133.5° C.

Anal. Calc'd for C$_{18}$H$_{28}$N$_4$O/C$_7$H$_5$NO$_3$S: C, 60.10; H, 6.66; N, 14.02 Found: C, 60.12; H, 6.69N, 13.95.

EXAMPLE 31

N-[1-Dimethylamino-3,3-dimethylbutylidene]-N'-phenyl-4-morpholinecarboximidamide(E)-2-butenedioate (2:3) Cpd 20

A solution of N,N-dimethyl-tert-butylacetamide (J. Org. Chem. 1970, 35, 1597-1602: 2.90 g, 22.5 mM) in methylene chloride (50 mL) was added to freshly prepared Et$_3$O(+)BF$_4$(−) (Et$_2$OBF$_3$ 35.3 mM, epichlorohydrin 26.5 mM, ether 100 mL) at room temperature under Ar. The reaction mixture was stirred at room temperature for 3 hours. A solution of guanidine derivative II (NR$_4$R$_5$=morpholine: 4.65 g, 22.5 mM) in methylene chloride (50 mL) was added to the reaction brew and stirred at room temperature for 72 hours. The mixture was concentrated in vacuo, partitioned between water and ether and the resulting solid was filtered. The solid was partitioned between 15% NaOH (aq) and methylene chloride. The organic layer was dried (K$_2$CO$_3$), filtered, and concentrated in vacuo. A solution of the residue (2.96 g) in EtOH (10 mL) was added to a solution of fumaric acid (1.04 g) in EtOH (15 mL). The title compound precipitated out of this mixture as a solid: mp 150°–152° C.

Anal. Calc'd for C$_{19}$H$_{30}$N$_4$O/1.5 C$_4$H$_4$O$_4$: C, 59.51; H, 7.19; N, 11.10 Found: C, 59.43; H, 7.15; N, 11.05.

EXAMPLE 32

N-[1-[[(4-Morpholinyl)(phenylimino)methyl]imino]ethyl]acetamide Cpd 32

Guanidine derivative II (NR$_4$R$_5$=morpholine:5.12 g, 25 mM) and N-acetylacetimidic acid ethyl ester (Chem Ber, 1985, 118, 3089-3104: 12.9 g, 100 mM) were stirred together at room temperature for 4 days. The resulting solid precipitate was separated and triturated with ether/cyclohexane to give the title compound as a solid: mp 146°–149° C.

Anal. Calc'd for C$_{15}$H$_{20}$N$_4$O$_2$: C, 62.48; H, 6.99; N, 19.43 Found: C, 62.43; H, 7.01; N, 19.39.

EXAMPLE 33

N-[Cyclohexyl(dimethylamino)methylene]-N'-phenyl-4-morpholinecarboximidamide (E)-2-Butenedioate (2:3) Cpd 12

A solution of N,N-dimethylcyclohexylacetamide (U.S. Pat. No. 4,835,312, May 30, 1989: 11.32 g, 73 mM) in methylene chloride (150 mL) was added to freshly prepared Et$_3$O(+)BF$_4$(−) (Et$_2$OBF$_3$ 114.5 mM, epichlorohydrin 85.9 mM, ether 200 mL) at room temperature under Ar. The reaction mixture was stirred at room temperature for 5 hours. A solution of guanidine derivative II (NR$_4$R$_5$=morpholine: 14.97 g, 73 mM) in methylene chloride (120 mL) was added to the reaction brew and stirred at room temperature for 72 hours. The resulting mixture was concentrated in vacuo and partitioned between water and ether. The aqueous phase was extracted with several portions of ether followed by several portions of methylene chloride. The combined methylene chloride layers were washed with successive portions of water and 15% NaOH (aq), dried (K$_2$CO$_3$), filtered, and concentrated in vacuo. The residue was dissolved in EtOH (40 mL), added to a solution of fumaric acid (4.01 g) in EtOH (50 mL). The title compound precipitated out of this solution as a solid: mp 169°–170.5° C.

Anal. Calc'd for C$_{20}$H$_{30}$N$_4$O/(3/2)C$_4$H$_4$O$_4$: C, 60.45; H, 7.02; N, 10.85 Found: C, 60.60; H, 7.17; N, 10.83.

EXAMPLE 34

N-[1-(Methylamino)propylidene]-N'-phenyl-4-morpholinecarboximidamide Cpd 29

Monomethylamine was bubbled into a solution of thiomethyl derivative V (R=Et NR$_4$R$_5$=morpholine: 3.47 g, 11.92 mM) in THF (100 mL) for 15 minutes and the resulting mixture was stirred at room temperature in a stopped flask for 3 days. The resulting mixture was concentrated in vacuo and partitioned between 15% NaOH (aq) and methylene chloride. The organic layer was dried (K$_2$CO$_3$), filtered, and concentrated in vacuo. The residue was crystallized from cyclohexane to give the title compound as a white solid: mp 117°–120° C.

Anal. Calc'd for C$_{15}$H$_{22}$N$_4$O: C, 65.67; H, 8.08; N, 20.42 Found: C, 65.70; H, 8.11; N, 20.26.

EXAMPLE 35

COMPOUND ACTIVITY EVALUATION

The compounds listed in Table 5 were tested for activity in a rat oral glucose tolerance test. Male Sprague-Dawley rats (200-275 grams) are given water ad libitum and fasted 18-24 hours prior to the experiment. Three to five rats are randomly assigned to each test and control group. Test compounds (2.5, 5.0, 10.0 mg/kg) are administered subcutaneously (0.5 mL) at 30 minutes prior to a standard oral glucose load (1 g/kg body weight). Control animals are given an equal amount of vehicle (H₂O or 0.5% hydroxypropyl methyl cellulose). Drug doses are calculated as the free base. Serial blood samples (0.1 milliliter) are obtained from the tail without anesthesia prior to (0 min) and at 30, 60, 90, 120, 150 and 180 minutes after glucose administration. Blood samples are immediately deproteinized with aqueous solutions of Ba(OH)₂ and ZnSO₄. and glucose concentrations in the supernatants are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point are expressed in terms of milligram percent (mg glucose/100 mL of blood). The mean glucose values of the controls are compared statistically by the unpaired Student's t-test to the means of the experimental group at each corresponding time point. If the compound lowers the blood glucose significantly at any time at a 95% confidence limit, the compound is considered to have hypoglycemic activity. The maximum % lowering of blood glucose from the corresponding mean values of the control group is determined for each rat in the experimental groups and used to calculate the mean maximum percent lowering of glucose from control. The ED 30 (dose producing a 30% decrease from control) and the 95% confidence intervals (CI) are determined from regression analysis of the mean maximum percent decrease from control vs log dose(mg/kg).

TABLE 5

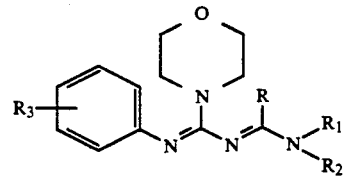

| Cpd # | R | R₁ | R₂ | R₃ | Mean Max % Low | ED₃₀(95% CI) |
|---|---|---|---|---|---|---|
| 1 | H | CH₃ | CH₃ | H | 22 | ND |
| 2 | Ph | CH₃ | CH₃ | H | 25 | ND |
| 3 | CH₃ | CH₃ | CH₃ | H | 38 | 6.7 (5.2-10.1) |
| 4 | CH₂CH₃ | CH₃ | CH₃ | H | 43 | 5.3 (3.3-9.1) |
| 5 | CH₃ | —(CH₂)₂— | —(CH₂)₃— | H | 46 | 5.3 (3.0-9.2) |
| 6 | i-Pr | CH₃ | CH₃ | H | 43 | 4.3 (3.0-5.6) |
| 7 | CH₃ | H | CH₃ | H | 45 | 2.6 (1.3-3.5) |
| 8 | n-hexyl | CH₃ | CH₃ | H | 31 | ND |
| 9 | CH₃ | CH₃ | n-Bu | H | 33 | 7.6 (5.2-20.8) |
| 10 | CH₃ | H | i-Pr | H | 42 | 3.9 (1.5-6.2) |
| 11 | CH₃ | CH₃ | Ph | H | 20 | ND |
| 12 | c-hexyl | CH₃ | CH₃ | H | 27 | ND |
| 13 | i-Pr | H | CH₃ | H | 52 | 1.5 (1.1-1.9) |
| 14 | Bzl | CH₃ | CH₃ | H | 27 | ND |
| 15 | CH₃ | Bzl | Ph | H | 17 | ND |
| 16 | CH₃ | H | Ph | H | 26 | ND |
| 17 | t-Bu | CH₃ | CH₃ | H | 40 | 9.5 (6.5-32) |
| 18 | i-Pr | H | i-Pr | H | 23 | ND |
| 19 | CH₃ | —(CH₂)₂O— | —(CH₂O)₂— | H | 24 | ND |
| 20 | CH₂-t-Bu | CH₃ | CH₃ | H | 37 | 5.9 (3-36) |
| 21 | CH₃ | H | t-Bu | H | 45 | 4.2 (1.9-6.6) |
| 22 | CH₃ | H | Bzl | H | 50 | 4.3 (2.3-6.4) |
| 23 | CH₃ | H | H | H | 21 | ND |
| 24 | CH₃ | H | n-Pr | H | 56 | 0.97 (0.06-1.9) |
| 25 | i-Pr | H | H | H | 34 | ND |
| 26 | i-Pr | Et | H | H | 26 | ND |
| 27 | i-Pr | n-Pr | H | H | 31 | ND |
| 28 | i-Pr | CH₃ | H | F | 42 | ND |
| 29 | Et | CH₃ | H | H | 42 | ND |
| 30 | CH₃ | Et | H | H | 48 | 4.6 (3.8-5.3) |
| 31 | CH₃ | (CH₂)₂OH | H | H | 15 | ND |
| 32 | CH₃ | C(O)CH₃ | H | H | 22 | ND |
| 33 | i-Pr | CH₃ | H | OCH₃ | 21 | ND |
| Comparative compound: Linogliride | | | | | 34 | 6.1 (4.3-8.1) |

For Cpds. 5 and 19 R₁ and R₂ are taken together to form an NR₁R₂ heterocyclic ring.

Mean maximum % lowering is calculated as described in Example 35. The values reported are determined at a dose of 10 mg/kg. ED₃₀ equals the dose calculated to produce a 30% decrease of glucose from control. The 95% confidence interval (CI) is shown in parentheses. ND=Not Determined.

The above test results demonstrate the utility of the compounds of the invention for decreasing the blood level of glucose in mammals (e.g. rats) thus demonstrating hypoglycemic activity.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methyl cellulose, sodium carbosyl methyl cellulose, and the like. Liquid form preparations include solutions which are suitable for oral or parenteral administration, or suspensions and emulsions suitable for oral administration. Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76-93, "Pharmaceutical Preparations and Their Manufacture", pp. 1409–1677 (1985).

In therapeutic use as hyperglycemic agents, the compounds utilized in the methods of this invention may be administered to a patient either orally (for those compounds which are orally active) or parenterally, preferably subcutaneously, at effective dosage levels of from about 30-1000 mg per day and preferably about 50-800 mg per day. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

The scope of the present invention is not limited by the description, examples and suggested uses described herein and modifications can be made without departing from the spirit of the invention. For example, additional medicaments or active components may be used in combination with the compounds of the invention. Further, the novel intermediate and hypoglycemic active compounds of the invention may have other uses in addition to those described herein. For example, the compounds of the invention may be useful for treatment of cardiovascular disease states.

Applications of the compounds, compositions and methods of the present invention for medical or pharmaceutical uses can be accomplished by any clinical, medical, and pharmaceutical methods and techniques as are presently or prospectively known to those skilled in the art. Thus it is intended that the present invention cover any modifications and variations of this invention provided that they come within the scope of the appended claims and their equivalents.

What is claimed is:

1. A compound of the formula:

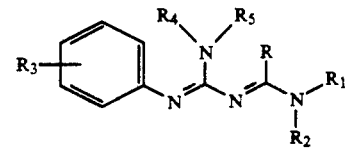

wherein:

R is selected from the group consisting of H, alkyl ($C_1$–$C_8$), branched alkyl ($C_3$–$C_5$) or cycloalkyl ($C_3$–$C_7$);

$R_1$ and $R_2$ are the same or different and are selected from the group consisting of hydrogen, alkyl ($C_1$–$C_5$), branched alkyl ($C_3$–$C_5$), cycloalkyl ($C_3$–$C_7$), aralkyl wherein the alkyl portion is $C_1$–$C_5$ or hydroxyalkyl and the aryl portion is phenyl or substituted phenyl wherein the substituents are selected from alkyl ($C_1$–$C_5$), alkoxy ($C_1$–$C_4$) and halogen, or $R_1R_2N$ may be taken together to form a heterocyclic ring containing N and 3-5 carbon atoms or said ring additionally contains one or more heteroatoms such as O or S;

$R_3$ is selected from the group consisting of hydrogen, alkyl ($C_1$–$C_5$), alkoxy ($C_1$–$C_4$) and halogen; and $R_4$ and $R_5$ are the same or different and are selected from the group consisting of alkyl ($C_1$–$C_5$), branched alkyl ($C_3$–$C_5$), cyclohexyl, cyclopentyl or $R_4R_5N$ is taken together to form a heterocyclic ring containing N and 3-5 carbon atoms or said ring additionally contains one or more heteroatoms such as O, N or S to form a heterocyclic ring selected from the group consisting of piperidino, morpholino, pyrrolidino and thiamorpholino; and pharmaceutically acceptable salts thereof.

2. A compound according to claim 1 of the formula:

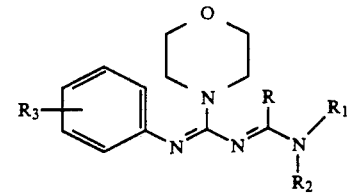

wherein R is selected from the group consisting of H, alkyl ($C_1$–$C_8$), branched alkyl ($C_3$–$C_5$), cycloalkyl ($C_3$–$C_7$), aryl and aralkyl wherein the aryl portion is phenyl or naphthyl and the alkyl portion is $C_1$–$C_5$;

$R_1$ and $R_2$ are the same or different and are selected from the group consisting of hydrogen, alkyl ($C_1$–$C_6$), branched alkyl ($C_3$–$C_4$), cyclohexyl ($C_3$–$C_7$), or NR, $R_2$ is then taken together as a heterocyclic ring containing N and 4 or 5 carbon atoms or additionally containing oxygen in the ring; and $R_3$ is H, F or methoxy.

3. A compound according to claim 1 selected from the group consisting of:
   N'-Phenyl-N-[1-(propylamino)ethylidene]-4-morpholinecarboximidamide;
   N-[1-(Methylamino)ethylidene]-N'-phenyl-4-morpholinecarboximidamide (E)-2-Butenedioate (2:3);
   N-[2-Methyl-1-(methylamino)propylidene]-N'-phenyl-4-morpholinecarboximidamide; and
   N-[1[(1-Methylethyl)amino]ethylidene]-N'-phenyl-4-morpholinecarboximidamide.

4. A compound according to claim 1 consisting of:
   N'-Phenyl-N-[1-(propylamino)ethylidene]-4-morpholinecarboximidamide.

5. A compound according to claim 1 consisting of:
   N-[1-(Methylamino)ethylidene]-N'-phenyl-4-morpholinecarboximidamide (E)-2-Butenedioate (2:3).

6. A compound according to claim 1 consisting of:
   N-[2-Methyl-1-(methylamino)propylidene]-N'-phenyl-4-morpholinecarboximidamide.

7. A method of treating hyperglycemia comprising the step of administering a therapeutically effective amount of a compound according to claim 1 to a patient in need of such treatment.

8. A method of treating hyperglycemia comprising the step of administering a therapeutically effective amount of a compound according to claim 2 to a patient in need of such treatment.

9. A method of treating hyperglycemia comprising the step of administering a therapeutically effective amount of a compound according to claim 3 to a patient in need of such treatment.

10. A method of treating hyperglycemia comprising the step of administering a therapeutically effective amount of a compound according to claim 4 to a patient in need of such treatment.

11. A method of treating hyperglycemia comprising the step of administering a therapeutically effective amount of a blood glucose lowering compound according to claim 1 to a patient in need of such treatment.

12. A method of treating hyperglycemia comprising the step of administering a therapeutically effective amount of a blood glucose lowering compound according to claim 2 to a patient in need of such treatment.

13. A method of treating hyperglycemia comprising the step of administering a therapeutically effective amount of a blood glucose lowering compound according to claim 3 to a patient in need of such treatment.

14. A method of treating hyperglycemia comprising the step of administering a therapeutically effective amount of a blood glucose lowering compound according to claim 4 to a patient in need of such treatment.

15. A pharmaceutical composition for treating hyperglycemia comprising a compound according to claim 1 and a pharmaceutically acceptable carrier.

* * * * *